(12) United States Patent  (10) Patent No.: US 8,529,595 B2
Voeller et al.  (45) Date of Patent: Sep. 10, 2013

(54) INTRAVASCULAR FILTER

(75) Inventors: Virgil Voeller, St. Louis Park, MN (US); Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1813 days.

(21) Appl. No.: 10/880,667

(22) Filed: Jun. 30, 2004

(65) Prior Publication Data

US 2006/0004402 A1  Jan. 5, 2006

(51) Int. Cl.
  *A61F 2/01* (2006.01)
(52) U.S. Cl.
  USPC ......................................................... 606/200
(58) Field of Classification Search
  USPC .................. 606/200, 113, 198, 108, 191, 194; 623/23.72
  See application file for complete search history.

(56) References Cited

U.S. PATENT DOCUMENTS

| | | | |
|---|---|---|---|
| 3,952,747 A | 4/1976 | Kimmell, Jr. | |
| 4,688,553 A | 8/1987 | Metals | |
| 5,059,205 A | 10/1991 | El-Nounou et al. | |
| 5,133,733 A | 7/1992 | Rasmussen et al. | |
| 5,242,462 A | 9/1993 | El-Nounou et al. | |
| 5,370,657 A | 12/1994 | Irie | |
| 5,375,612 A | 12/1994 | Cottenceau et al. | |
| 5,383,887 A | 1/1995 | Nadal | |
| 5,725,550 A | 3/1998 | Nadal | |
| 5,746,767 A | 5/1998 | Smith | |
| 5,853,420 A * | 12/1998 | Chevillon et al. | 606/200 |
| 5,968,071 A | 10/1999 | Chevillon et al. | |
| 5,984,947 A | 11/1999 | Smith | |
| 6,007,558 A | 12/1999 | Ravenscroft et al. | |
| 6,013,093 A | 1/2000 | Nott et al. | |
| 6,080,178 A | 6/2000 | Meglin | |
| 6,126,673 A | 10/2000 | Kim et al. | |
| 6,193,739 B1 | 2/2001 | Chevillon et al. | |
| 6,231,589 B1 | 5/2001 | Wessman et al. | |
| 6,273,900 B1 | 8/2001 | Nott et al. | |
| 6,273,901 B1 | 8/2001 | Whitcher et al. | |
| 6,416,530 B2 | 7/2002 | DeVries et al. | |
| 6,468,290 B1 | 10/2002 | Weldon et al. | |
| 6,517,559 B1 | 2/2003 | O'Connell | |
| 6,582,447 B1 | 6/2003 | Patel et al. | |
| 6,706,054 B2 | 3/2004 | Wessman et al. | |
| 2003/0176888 A1* | 9/2003 | O'Connell | 606/200 |
| 2005/0107822 A1 | 5/2005 | WasDyke | |
| 2005/0209632 A1* | 9/2005 | Wallace | 606/200 |

* cited by examiner

*Primary Examiner* — Kathleen Holwerda
(74) *Attorney, Agent, or Firm* — Seager, Tufte & Wickhem LLC

(57) ABSTRACT

An intravascular filter provides filtering capacity while retaining desired blood flow. An illustrative filter can include a first filter leg and a second filter leg, each of which have a free end and an opposite joined end. The joined end of each filter leg is secured to a center hub. A first portion of each filter leg extends in a first direction while a second portion of each filter leg extends in a second direction. An apex is positioned between the first and second portions of each filter leg.

21 Claims, 6 Drawing Sheets

INTRAVASCULAR FILTER

TECHNICAL FIELD

The present invention relates generally to intravascular filters. More specifically, the present invention relates to implantable intravascular filters.

BACKGROUND

Intravascular filters can be used to treat vascular conditions such as pulmonary embolism. These devices can be inserted intravenously into a target location of the body such as an artery or vein, and can capture blood clots (emboli) contained in the blood stream before they can reach the heart and/or lungs and cause permanent damage to the body. An intravascular filter can be placed percutaneously via an introducer sheath through the femoral arteries or the jugular vein using a local anesthetic, or by performing a laparotomy with the patient under general anesthesia.

A variety of intravascular filters such as vena cava filters are known. However, a need remains for improved designs. A need remains for vena cava filters that provide desired filtering and enhanced blood flow through the vasculature in which the filter is deployed.

SUMMARY

The present invention is directed to an intravascular filter that provides filtering capacity while maintaining desired blood flow.

Accordingly, an illustrative embodiment of the present invention can be found in an intravascular filter that has a pair of filter legs including a first filter leg and a second filter leg. Each of the first and second filter legs have a free end and an opposite joined end. The joined end of each filter leg is secured to a center hub. A first portion of each filter leg extends in a first direction while a second portion of each filter leg extends in a second direction. An apex is positioned between the first and second portions of each filter leg. The second portion of the first filter leg is not parallel with the second portion of the second filter leg when the filter is in a deployed configuration.

Another illustrative embodiment of the present invention can be found in an intravascular filter that has a number of filter legs, with each filter leg having a first end, a second end and an apex positioned between the first end and the second end. The first end of each filter leg is joined to a center hub. A first portion of each filter leg extends between the first end of the filter leg and the apex while a second portion of each filter leg extends between the apex and the second end of each filter leg. The first portion of each filter leg extends at an angle α defined as an acute angle between the first portion of the filter leg and a longitudinal axis extending through the center hub. The second portion of each filter leg extends at an angle β defined as an acute angle between the first portion of the filter leg and the second portion of the filter leg such that β is greater than α.

Another illustrative embodiment of the present invention can be found in an intravascular filter that has a pair of filter legs, with each filter leg having a first end, a second end and an apex positioned between the first end and the second end. The first end of each filter leg is joined to a center hub. A first portion of each filter leg extends between the first end of the filter leg and the apex while a second portion of each filter leg extends between the apex and the second end of the filter. The first portion of each filter leg extends at an angle α as defined above. The second portion of each filter leg extends at an angle γ defined as an acute angle between the second portion of the filter leg and a second longitudinal axis extending through the apex and parallel to the first longitudinal axis such that γ is greater than 0.

Another illustrative embodiment of the present invention can be found in an intravascular filter that has a pair of filter legs, with each filter leg having a first end, a second end and an apex positioned between the first end and the second end. The first end of each filter leg is joined to a center hub. A first portion of each filter leg extends between the first end of the filter leg and the apex while a second portion of each filter leg extends between the apex and the second end of the filter. The first portion of each filter leg extends at an angle θ defined as an angle between the first portion of the first filter leg and the first portion of the second filter leg. The second portion of each filter leg extends at an angle β as defined above such that β is greater than θ/2.

Another illustrative embodiment of the present invention can be found in a method of capturing embolic debris. An intravascular filter having a center and an opposing periphery can be provided. Emboli deflecting means are positioned near the center of the filter while emboli capturing means are positioned at the periphery of the filter. The intravascular filter can be deployed such that the emboli deflecting means are upstream of the emboli capturing means.

The above summary of the present invention is not intended to describe each disclosed embodiment or every implementation of the present invention. The Figures and Detailed Description which follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
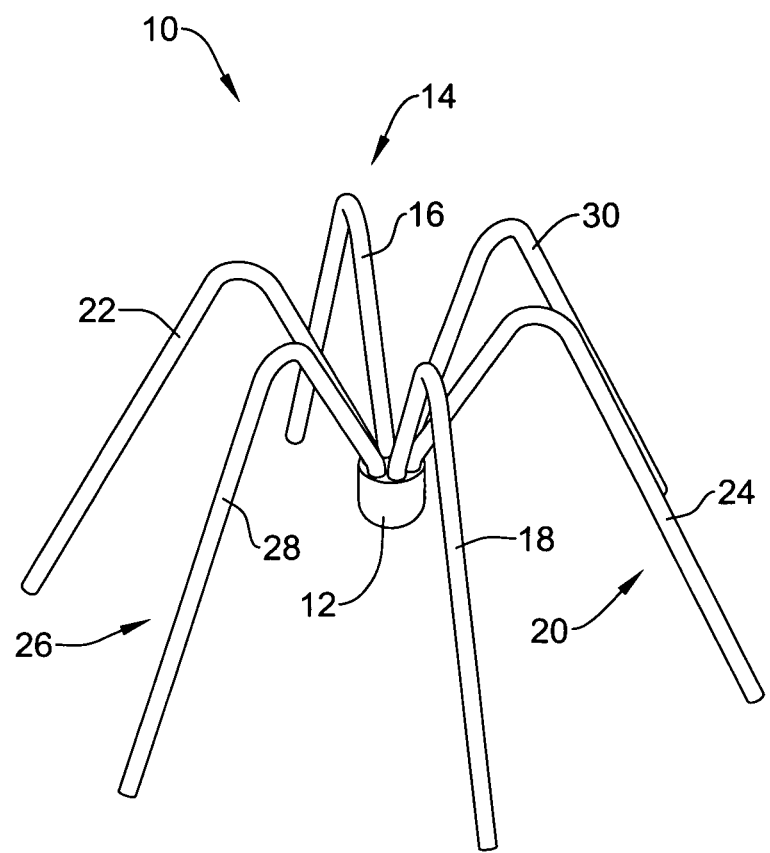
FIG. 1 is a perspective view of an unconstrained intravascular filter in accordance with an illustrative embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

FIG. 1 is a perspective view of an intravascular filter 10. For illustrative but non-limiting purposes, the present invention will be described with respect to vena cava filters. The intravascular filter 10 includes a center hub 12 and can include one or more pairs of filter legs extending from the center hub 12. In the illustrated embodiment, the intravascular filter 10 includes three pairs of filter legs. In particular, the intravascular filter 10 includes a first pair 14 of filter legs 16 and 18, a second pair 20 of filter legs 22 and 24, and a third pair 26 of filter legs 28 and 30. In other embodiments, however, the intravascular filter 10 can include one, two, four, five or more pairs of filter legs that can each be spaced equidistantly about the center hub 12.

The intravascular filter 10 can be formed of any suitable material. In some embodiments, it can be useful to form the intravascular filter 10 of a metallic material that permits compression of the intravascular filter 10 into a delivery configuration while allowing the intravascular filter 10 to regain its deployment configuration after the intravascular filter 10 has been deployed. Suitable metals include platinum, gold, tantalum, tungsten, titanium, or stainless steel, and shape memory materials such as nickel-titanium alloys. In particular, the intravascular filter 10 can be formed of nickel-titanium alloys, stainless steel enriched with platinum, MP35N, cobalt-chromium-nickel-molyodenum-iron alloy specified by ASTM F1058 and ISO 5832-7 or other suitable material.

In some embodiments, each of the filter legs 16, 18, 22, 24, 28 and 30 (as illustrated in FIG. 1) can be independently formed and can subsequently be secured to the center hub 12. The filter legs 16, 18, 22, 24, 28 and 30 can each be formed by bending or otherwise shaping a suitably sized wire having any suitable cross-section. In some embodiments, the filter legs 16, 18, 22, 24, 28 and 30 can each be formed from a wire having a round cross-section and a diameter that is in the range of about 0.001" to about 0.050".

The filter legs 16, 18, 22, 24, 28 and 30 can be welded or bonded to the center hub 12. In some embodiments, the center hub 12 can include apertures (not expressly shown) into which the filter legs 16, 18, 22, 24, 28 and 30 can be inserted. In other embodiments, each pair 14, 20 and 26 of filter legs can be formed by bending or shaping a suitably sized wire, i.e. the filter leg 16 and the filter leg 18, for example, can together be formed from a single length of wire.

Figure 2:
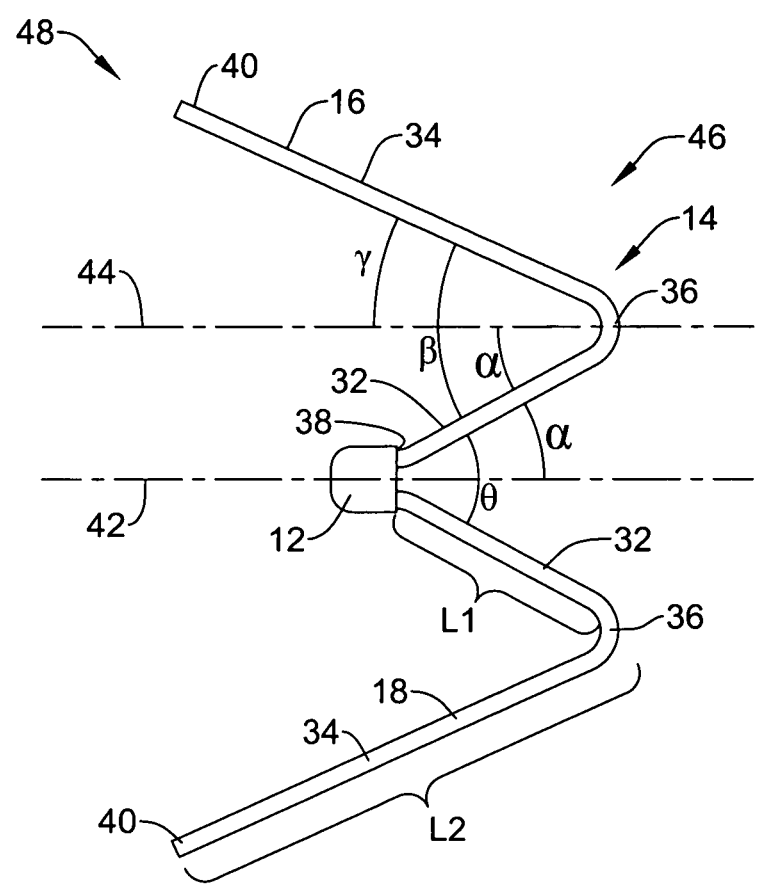
FIG. 2 is a side view of the unconstrained intravascular filter of FIG. 1.

FIG. 2 is a side elevation of a portion of the intravascular filter 10. In particular, FIG. 2 shows the geometric relationships between the center hub 12 and the first pair 14 of filter legs 16 and 18. Similar relationships can exist between the center hub 12 and the second pair 20 of filter legs 22 and 24, the center hub 12 and the third pair 26 of filter legs 28 and 30, or between the center hub 12 and additional (not shown) pairs of filter legs.

As shown in FIG. 2, the filter leg 16 and the filter leg 18 each have a first portion 32, a second portion 34 and an apex 36 that is positioned between the first portion 32 and the second portion 34. The first portion 32 extends between a first end 38 and the apex 36. The second portion 34 extends from the apex 36 to a second end 40. In some embodiments, the second portion 34 can be as long as or even longer than the first portion 32. In particular, the first portion 32 can have a length, designated in FIG. 2 as "L1", that is in the range of 0.1 inches to about 3 inches. Similarly, the second portion 34 can have a length, designated in FIG. 2 as "L2", that is in the range of about 0.25 inches to about 6 inches.

As shown, a first longitudinal axis 42 can be envisioned as extending through the intravascular filter 10, traversing the center hub 12. A second longitudinal axis 44, which can be considered as parallel with the first longitudinal axis 42, extends through the intravascular filter 10, traversing the apex 36. In some embodiments, the intravascular filter 10 can be considered as having a first side 46 corresponding to a side of the intravascular filter 10 closest to the apex 36 of each filter leg 16 and 18 (as illustrated) and a second side 48 corresponding to a side of the intravascular filter 10 closest to the second end 40 of each filter leg 16 and 18. Each of the first longitudinal axis 42 and the second longitudinal axis 44 can be considered as extending from the first side 46 to the second side 48.

A number of angles can be defined with respect to FIG. 2. The first portion 32 of the filter leg 16 forms an acute angle α with the first longitudinal axis 42. Because the first and second longitudinal axes 42 and 44 are parallel, the second portion 34 of the filter leg 16 forms the same acute angle α with the second longitudinal axis 44. The first portion 32 of the filter leg 16 forms an acute angle β with the second portion 34 of the filter leg. It can be seen that the angle γ is equal to β minus α. The first portion 32 of the filter leg 16 forms an angle θ with the first portion 32 of the filter leg 18. In particular embodiments, the intravascular filter 10 can be considered as being symmetric about the first longitudinal axis 42. As a result, the angle θ can be considered as being twice the angle α.

In some embodiments, the first portion 32 of the filter leg 16 can extend in a first direction that includes an axial component that extends in a first axial direction. The second portion 34 of the filter leg 16 can extend in a second direction that includes an axial component that extends in an axial direction that is opposite that of the first portion 32. In this, an axial component can be considered as parallel with either of the first longitudinal axis 42 or the second longitudinal axis 44. In some cases, the second portion 34 of filter leg 16 may be not parallel with the second portion 34 of filter leg 18. Furthermore, in some cases, the second portion 34 of all the filter legs 16, 18, 22, 24, 28, and 30 may be not parallel with each other.

In some embodiments, β can be greater than α. In particular embodiments, β can be at least about 10 degrees greater than α. In particular embodiments, β can be at least about 20 degrees greater than α. In some embodiments, β can be in the range of about 12 to about 25 degrees. Similarly, as θ can be considered as equal to twice α, in some embodiments, β can be about 10 or even about 20 degrees greater than θ/2. In some embodiments, γ can be greater than zero. In particular embodiments, γ can be at least about 10 degrees. In particular embodiments, γ can be about 20 degrees.

Figure 3:
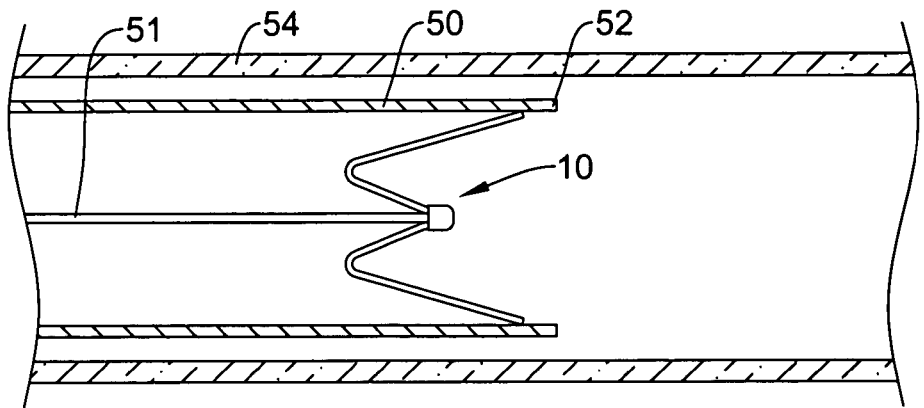
FIG. 3 is a partial cross-sectional view of the intravascular filter of FIG. 1, shown in delivery configuration within an introducer sheath.
Figure 4:
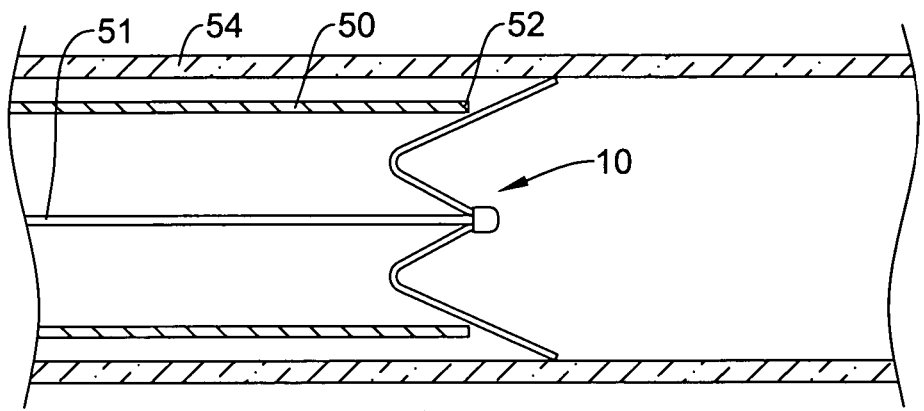
FIG. 4 is a partial cross-sectional view of the intravascular filter of FIG. 1, shown partially deployed.
Figure 5:
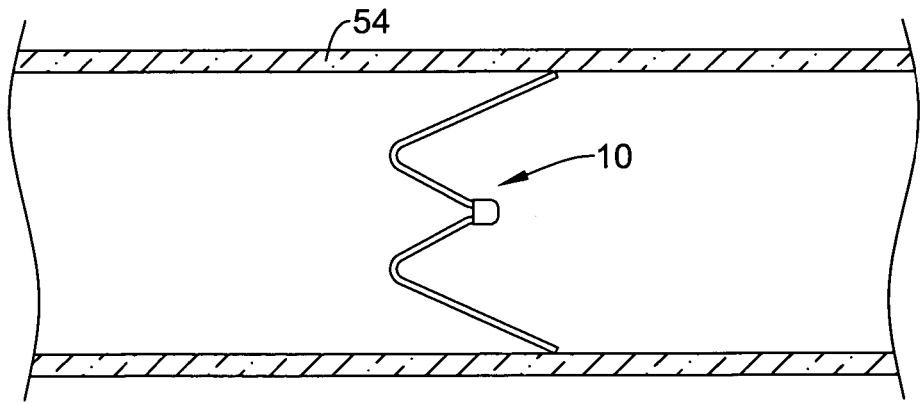
FIG. 5 is a partial cross-sectional view of the intravascular filter of FIG. 1, shown deployed.

FIGS. 3 through 5 illustrate deployment of the intravascular filter 10. In FIG. 3, the intravascular filter 10 is schematically illustrated in a collapsed or delivery configuration within an introducer sheath 50 having a distal end 52. In some embodiments, the intravascular filter 10 can be delivered to the physician or other healthcare professional preloaded into the introducer sheath 50. In other embodiments, it is considered that the intravascular filter 10 can be loaded into the introducer sheath 50 just prior to insertion of the introducer sheath 50 into a vessel 54.

In FIG. 4, the intravascular filter 10 has been moved distally within the introducer sheath 50 and is positioned near the distal end 52 of the introducer sheath 50. The intravascular filter 10 can be moved distally using any conventionally known technique. For example, a pusher sheath 51 can be positioned within the introducer sheath 50 and can be used to push against the intravascular filter 10 to urge the intravascular filter 10 distally. In some embodiments, the pusher sheath 51 can hold the intravascular filter 10 while the introducer sheath 50 is withdrawn proximally in order to deploy the intravascular filter 10. In some embodiments, a pressurized fluid such as saline may be used to urge the intravascular filter 10 distally. FIG. 5 illustrates the intravascular filter 10 in a fully deployed configuration.

Figure 6:
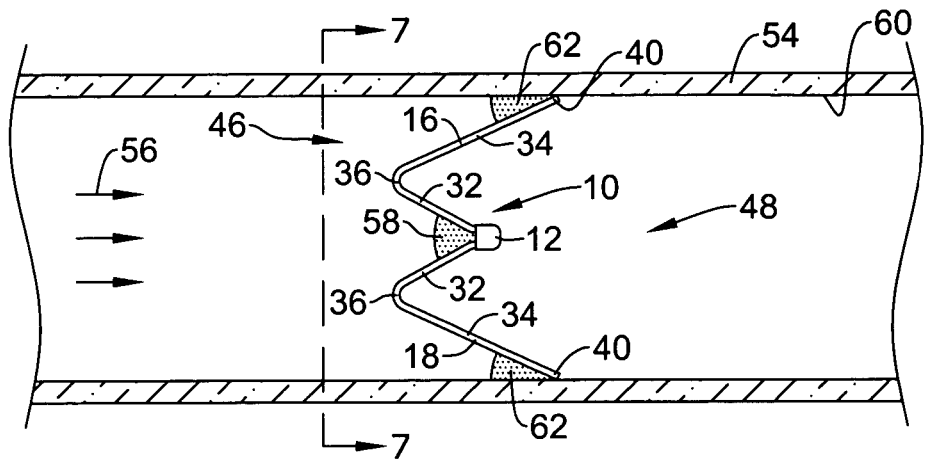
FIG. 6 is a partial cross-sectional view of the intravascular filter of FIG. 1, illustrating debris capture with blood flow in a first direction.

FIG. 6 illustrates the intravascular filter 10 deployed within a patient's vessel 54 such that the first side 46 of the intravascular filter 10 is upstream relative to the second side 48, as blood flow direction is indicated by arrows 56. The intravascular filter 10 is deployed such that the second end 40 of each filter leg 16 and 18 contacts an interior wall 60 of the vessel 54. In some embodiments, the second end 40 of each filter leg 16 and 18 (as illustrated) will contact the interior wall 60 of the vessel 54 with sufficient force to hold the intravascular filter 10 in place. In other embodiments, the second end 40 of each filter leg 16 and 18 can include a hook, barb or other holding structure (not illustrated) as is known in the art.

As blood clots or other emboli move downstream within the vessel 54, they intersect the first side 46 of the intravascular filter 10. Some of the debris, indicated in the Figure as reference number 58, may become lodged near the center of the intravascular filter 10. The first portion 32 of each of the filter leg 16 and the filter leg 18 can hold the debris in position. Some of the debris can be swept closer to the interior wall 60 of the vessel 54 and can form a roughly annular ring of debris 62 that is held in place in part by the interior wall 60 of the vessel 54 and the second portion 34 of the filter leg 16 and the filter leg 18.

The relative size of the annular ring of debris 62 can be modified or controlled by changing or controlling the relative angle between the second portion 34 of the filter legs 16 and 18 and the interior wall 60 of the vessel 54. This relative angle can be controlled by modifying the angles α, β, γ and θ as previously described. For example, increasing β can result in a relatively wider debris ring 62 as the second portion 34 of the filter leg 16 or 18 will form an increased acute angle with the interior wall 60 of the vessel 54.

Figure 7:
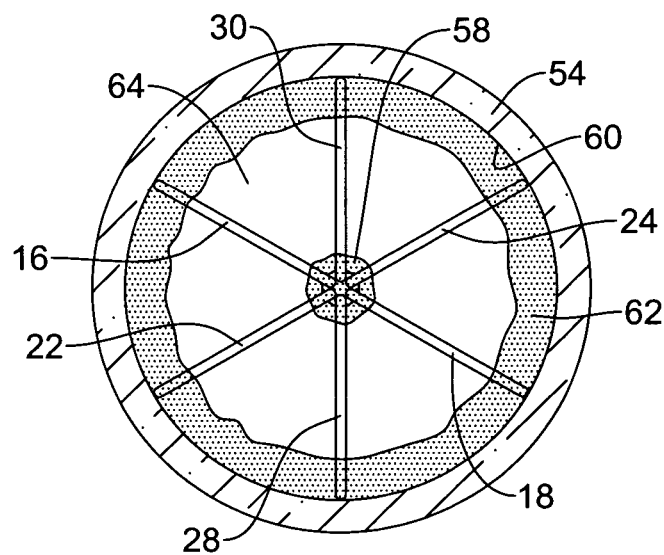
FIG. 7 is a cross-section taken along line 7-7 of FIG. 6.

FIG. 7 is a cross-section taken along line 7-7 of FIG. 6. By concentrating debris 58 near the center of the intravascular filter 10 and debris 62 near the periphery of the intravascular filter 10, a significant portion of the vessel 54 remains open to blood flow. This is indicated as free space 64 in FIG. 7.

Figure 8:
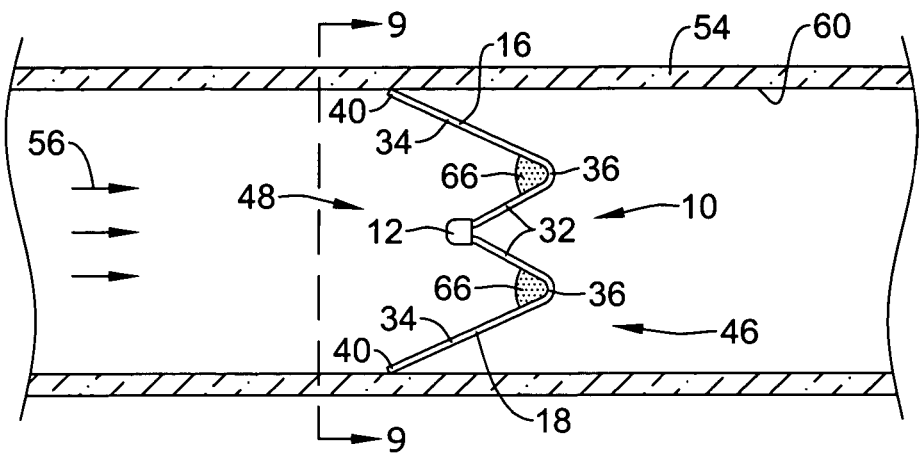
FIG. 8 is a partial cross-sectional view of the intravascular filter of FIG. 1, illustrating debris capture with blood flow in a second direction.
Figure 9:
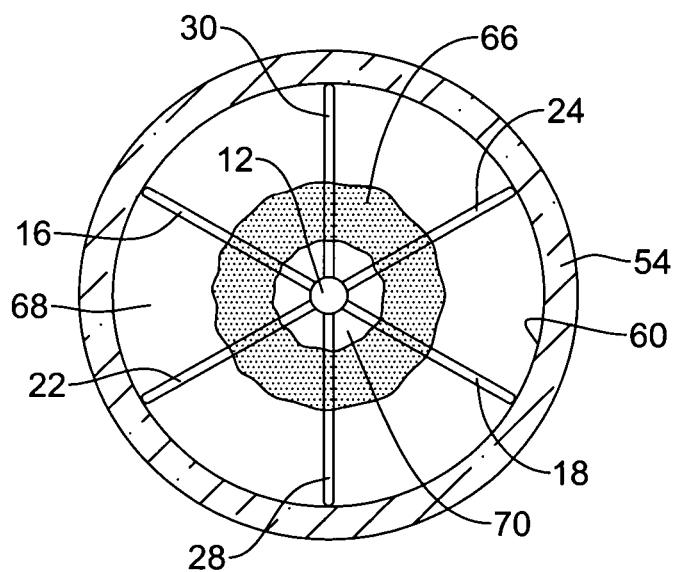
FIG. 9 is a cross-section taken along line 9-9 of FIG. 8.

In another embodiment, as illustrated in FIGS. 8 and 9, the intravascular filter 10 can be deployed such that its second side 48 is upstream relative to the first side 46, as blood flow direction is indicated by arrows 56. As blood clots or other emboli move downstream within the vessel 54, they intersect the second side 48 of the intravascular filter 10. Some of the debris, indicated in the Figure as reference number 66, may become lodged near the apex 36 of each filter leg 16 and 18 (as illustrated).

FIG. 9 is a cross-section taken along line 9-9 of FIG. 8. By concentrating debris 66 in a roughly annular ring, a significant portion of the vessel 54 remains open to blood flow. This is shown in the Figure as free space 68 and free space 70.

Figure 10:
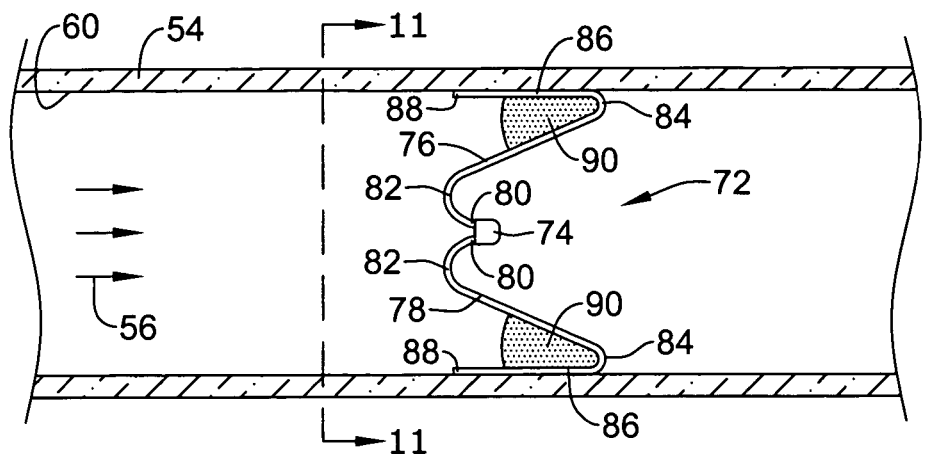
FIG. 10 is a partial cross-sectional view of another illustrative embodiment of an intravascular filter in accordance with the present invention, shown deployed within a vessel.
Figure 11:
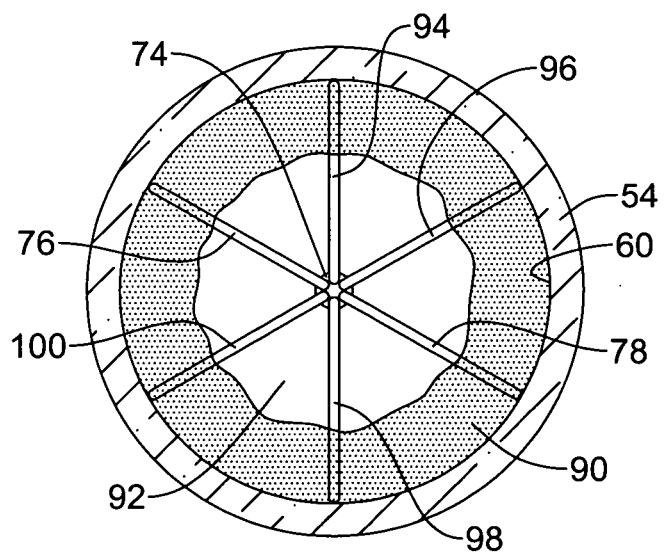
FIG. 11 is a cross-section taken along line 11-11 of FIG. 10.

Turning now to FIGS. 10 and 11, another embodiment of an intravascular filter 72 is shown deployed within a vessel 54. As illustrated, the intravascular filter 72 has a center hub 74, a first filter leg 76 and a second filter leg 78. However, the intravascular filter 72 can have two, three, four or more pairs of filter legs that can be spaced equidistantly about the center hub 74. Only two filter legs 76 and 78 are shown for ease of illustration.

The filter leg 76 and filter leg 78 each have a first end 80 attached to the center hub 74, a curved portion 82 that extends to an apex 84 and a straight portion 86 that extends from the apex 84 to a second end 88. The straight portion 86 contacts the interior wall 60 of the vessel 54 and thus can hold the intravascular filter 72 in place. In some embodiments, however, the straight portion 86 of each filter leg can include hooks or barbs to assist in anchoring the intravascular filter 72.

The intravascular filter 72 is deployed within the vessel 54 such that the curved portion 82 is upstream relative to the apex 84 of each filter leg 76 and 78, as blood flow direction is indicated by arrows 56. As blood clots or other emboli move downstream within the vessel 54, they intersect the intravascular filter 72. Debris, indicated in the Figure as reference number 90, can migrate to the periphery of the intravascular filter 72. In some embodiments, the curved portion 82 of each filter leg 76 and 78 can deflect debris towards the periphery of the intravascular filter 72. In some embodiments, the apex 84 and straight portion 86 of each filter leg 76 and 78 can serve to capture and hold debris.

FIG. 11 is a cross-section taken along line 11-11 of FIG. 10. By concentrating debris 90 in a roughly annular ring relatively near the interior wall 60 of the vessel 54, a significant portion of the vessel 54 remains open to blood flow. This is indicated as free space 92 in the Figure. Note that in FIG. 11, the intravascular filter 72 includes additional filter legs 94, 96, 98 and 100.

In each illustrated embodiment, the filter legs forming each of the intravascular filter 10 and 72 provide a surface upon which blood clots (emboli) can be collected. To facilitate lysing of the collected blood clots, all or a portion of the intravascular filters 10 and 72 can include an anti-thrombogenic coating such as herapin (or its derivatives), urokinase, or PPack (dextrophenylalanine proline arginine chloromethylketone).

If desired, an anti-inflammatory agent such as dexamethasone, prednisolone, corticosterone, budesonide, estrogen, sulfasalazine, mesalamine, or any suitable combination or mixture thereof may also be applied to the intravascular filter 10 and 72 to prevent inflammation caused by the engagement of the intravascular filter 10 and 72 along the vessel 54.

The invention should not be considered limited to the particular examples described above, but rather should be understood to cover all aspects of the invention as set out in the attached claims. Various modifications, equivalent processes, as well as numerous structures to which the invention can be applicable will be readily apparent to those of skill in the art upon review of the instant specification.

We claim:

1. An intravascular filter, comprising:
    at least two filter legs comprising a first filter leg and a second filter leg, each filter leg having a free end and an opposite joined end,
    wherein each filter leg has an unconstrained configuration, a delivery configuration, and a deployed configuration;
    a center hub, and a filter axis extending through the hub, the joined end of each filter leg secured to the center hub, each filter leg extending from the center hub, each of the filter legs having a first portion extending generally in a first axial direction, a second portion generally extending in a second opposite axial direction, and an apex positioned between the first portion and the second portion at which an acute angle is formed between the first and second portions such that the center hub is disposed axially between the apex and the free end of each of the at least two filter legs;
    wherein the first portion extends between the center hub and the apex;
    the acute angle is defined by an angle β defined as an angle between the first portion of the filter leg and the second portion of the filter leg;
    an angle α defined as an angle between the first portion of the filter leg and a longitudinal axis extending through the center hub; and
    wherein the filter is biased to expand from a delivery configuration to an unconstrained configuration wherein angle β is greater than angle α in the unconstrained configuration.

2. The intravascular filter of claim 1, further comprising a third filter leg and a fourth filter leg.

3. The intravascular filter of claim 2, wherein each of the third filter leg and the fourth filter leg have a first portion extending in a first direction, a second portion extending in a second direction, and an apex positioned therebetween, and the second portion of the third filter leg is not parallel with the second portion of the fourth filter leg.

4. The intravascular filter of claim 3, wherein none of the second portion of the first filter leg, the second portion of the second filter leg, the second portion of the third filter leg and the second portion of the fourth filter leg are parallel.

5. The intravascular filter of claim 1, wherein the intravascular filter has a deployed configuration in which the free end of each filter leg is positioned proximate a vessel wall.

6. The intravascular filter of claim 1, wherein the intravascular filter has a deployed configuration in which only the free end of each filter leg contacts a vessel wall.

7. The intravascular filter of claim 1, wherein each filter leg is bent, at each apex, at an angle of less than 90 degrees between the first portion and the second portion.

8. An intravascular filter, comprising:
    a plurality of filter legs, each filter leg having a first end, a second end and an apex positioned between the first end and the second end;
    a center hub, the first end of each filter leg joined to the center hub;
    each filter leg having a first generally straight portion extending between the first end and the apex;
    each filter leg having a second generally straight portion extending between the apex and the second end,
    wherein each filter leg has an unconstrained configuration, a delivery configuration, and a deployed configuration;
    the first portion of each filter leg in the unconstrained position extending at an angle α defined as an acute angle between the first portion of the filter leg and a longitudinal axis extending through the center hub;
    the second portion of each filter leg in the unconstrained position extending at an angle β defined as an acute angle between the first portion of the filter leg and the second portion of the filter leg; and
    wherein the filter is biased to expand from a delivery configuration to an unconstrained configuration wherein β is greater than α in the unconstrained configuration.

9. The intravascular filter of claim 8, wherein the apex of each filter leg defines a first side of the intravascular filter, the second end of each leg defines a second side of the intravascular filter, and wherein the longitudinal axis extends from the first side to the second side.

10. The intravascular filter of claim 8, wherein β is at least about 10 degrees greater than α.

11. The intravascular filter of claim 8, wherein β is at least about 20 degrees greater than α.

12. The intravascular filter of claim 8, wherein the first portion of each filter leg has a first length, the second portion of each filter leg has a second length, and the second length is equal to or greater than the first length.

13. The intravascular filter of claim 12, wherein the second length is greater than the first length.

14. An intravascular filter, comprising:
    a pair of filter legs, each filter leg having a first end, a second end and an apex positioned between the first end and the second end;
    a center hub, the first end of each filter leg joined to the center hub;
    each filter leg having a generally straight first portion extending between the first end and the apex;
    each filter leg having a generally straight second portion extending between the apex and the second end;
    the first portion of each filter leg having an unconstrained configuration in which the leg extends at an angle α defined as an acute angle between the first portion of the filter leg and a first longitudinal axis extending through the center hub;
    the second portion of each filter leg having an unconstrained configuration in which the leg extends an angle γ defined as an acute angle between the second portion of the filter leg and a second longitudinal axis extending through the apex and parallel to the first longitudinal axis; and
    the filter is biased to expand from a first to a second biased position wherein γ is greater than 0 in the unconstrained configuration.

15. The intravascular filter of claim 14, wherein the apex of each filter leg defines a first side of the intravascular filter, the second end of each leg defines a second side of the intravascular filter, and wherein the first and second longitudinal axes extend from the first side to the second side.

16. The intravascular filter of claim 14, wherein γ is greater than about 10 degrees.

17. The intravascular filter of claim 14, wherein γ is greater than about 20 degrees.

18. An intravascular filter, comprising:
- a pair of filter legs symmetrically disposed about a first longitudinal axis comprising a first filter leg and a second filter leg, each filter leg having a first end, a second end and an apex positioned between the first end and the second end;
- a center hub, the first end of each filter leg joined to the center hub;
- each filter leg having a first portion extending between the first end and the apex;
- each filter leg having a second portion extending between the apex and the second end such that the center hub is axially disposed between the apex and the second end of each filter leg;
- the first portion of each filter leg extending at an angle θ defined as an angle between the first portion of the first filter leg and the first portion of the second filter leg;
- the second portion of each filter leg extending at an angle β defined as an acute angle between the first portion of the filter leg and the second portion of the filter leg; and
- the filter is biased to expand from a first to a second biased position wherein β is greater than θ/2 in the second biased position.

19. The intravascular filter of claim 18, wherein β is at least about 10 degrees greater than θ/2.

20. The intravascular filter of claim 18, wherein β is at least about 20 degrees greater than θ/2.

21. A method of capturing embolic debris within a vasculature, comprising steps of:
- providing an intravascular filter having a center portion and an opposing periphery portion, further comprising the steps of:
    - deflecting emboli with the center portion positioned near the center of the filter; and
    - capturing emboli with the opposing periphery portion positioned at the periphery of the filter; and
- deploying the intravascular filter within the vasculature;
- wherein the intravascular filter is deployed within the vasculature such that the center portion is upstream of the opposing periphery portion, the intravascular filter having an unconstrained configuration comprising:
    - one or more pairs of filter legs, each filter leg having a first portion forming the center portion and a second portion forming the opposing periphery portion;
    - an angle β defined as an angle between the first portion of the filter leg and the second portion of the filter leg;
    - an angle α defined as an angle between the first portion of the filter leg and a longitudinal axis extending through the center hub; and
- wherein the filter is biased to expand from a first to a second biased position wherein angle β is greater than angle α in the second biased position.

* * * * *

UNITED STATES PATENT AND TRADEMARK OFFICE
CERTIFICATE OF CORRECTION

PATENT NO. : 8,529,595 B2
APPLICATION NO. : 10/880667
DATED : September 10, 2013
INVENTOR(S) : Virgil Voeller and Tracee Eidenschink It is certified that error appears in the above-identified patent and that said Letters Patent is hereby corrected as shown below:

In the Claims

Claim 8, Column 8, Line 23: delete "greater than a" and insert -- greater than α --.

Signed and Sealed this
Fifth Day of November, 2013

Teresa Stanek Rea
*Deputy Director of the United States Patent and Trademark Office*